(12) United States Patent
Mateczun et al.

(10) Patent No.: US 6,610,531 B1
(45) Date of Patent: Aug. 26, 2003

(54) VIABLE DRIED BACTERIA PRODUCED BY DRYING IN THE PRESENCE OF TREHALOSE AND DIVALENT CATION

(75) Inventors: Alfred J. Mateczun, Albuquerque, NM (US); Leonard F. Peruski, Jr., Dearborn, MI (US)

(73) Assignee: The United States of America as represented by the Secretary of the Navy, Washington, DC (US)

( * ) Notice: Subject to any disclaimer, the term of this patent is extended or adjusted under 35 U.S.C. 154(b) by 0 days.

(21) Appl. No.: 09/159,568

(22) Filed: Sep. 24, 1998

(51) Int. Cl.[7] .................. A61K 45/00; A01N 63/00; C12N 1/00; C12N 1/12; C12N 1/20
(52) U.S. Cl. .................. 435/260; 424/93.4; 424/282.1; 435/252.1; 435/252.33; 435/822; 435/849; 435/879; 435/909
(58) Field of Search .................. 435/243, 252.1, 435/822, 252.33, 260, 849, 879, 909; 424/93.1, 93.4, 282.1, DIG. 6

(56) References Cited

U.S. PATENT DOCUMENTS 4,875,921 A * 10/1989 Paau .................. 71/7
5,695,541 A * 12/1997 Kosanke et al. .................. 71/7
5,800,978 A * 9/1998 Goodrich, Jr. et al. .......... 435/2

FOREIGN PATENT DOCUMENTS

EP    0120111 A1  *  3/1984

* cited by examiner

Primary Examiner—David M. Naff
Assistant Examiner—Deborah K. Ware
(74) Attorney, Agent, or Firm—Joseph K. Hemby, Jr.; Charles H. Harris

(57) ABSTRACT

A method is provided for preserving live bacteria by subjecting an aqueous system containing the growing bacteria to drying without special equipment, in the presence of trehalose with or without the addition of divalent cations as stabilizing agents. Further, a dried composition for preservation of aerobic bacteria in a viable state is provided. The dried composition consists essentially of dried viable aerobic bacteria and an appropriate growth medium. The bacteria and growth medium are initially placed in an aqueous solution of 10 mM to 200 mM trehalose and a divalent cation, and dried at room temperature.

13 Claims, 1 Drawing Sheet

Preservation Procedure

Inoculate appropriate volume of media with actively growing bacteria → Incubate overnight → Add equal volume of "preservation media" → Dry cultures in incubator → Cover and store at room temperature → Rehydrate with water to recover bacteria with the genetic Characteristics of the original bacteria

VIABLE DRIED BACTERIA PRODUCED BY DRYING IN THE PRESENCE OF TREHALOSE AND DIVALENT CATION

FIELD OF THE INVENTION

This invention relates to a method of preserving bacteria for long-term storage without causing changes to the characteristics of the organism. More particularly, this invention relates to a method of preserving the bacteria by drying the bacteria in the presence of a preservative.

DESCRIPTION OF THE PRIOR ART

The maintenance of live bacteria in a stable form is critical for the conduct of basic microbiological studies and the development and production of diagnostic assays and vaccines. Furthermore, transport of bacterial strains between research or production facilities often requires the organisms to be in a preserved state to prevent damage or genetic alteration. Several methods exist for the preservation of bacterial cells. The two most widely used methods are freeze-drying (Crowe and Crowe 1991; Crowe et al., 1992) and desiccation (Carpenter et al., 1987 and 1988; Oliver et al., 1995; Roser, 1991; Shier, 1988). Methods for the freeze-drying of prokaryotic organisms, e.g. bacteria, has been relatively successful. Because successfully freeze-dried cells can be stored in the absense of freezing conditions, these procedures are more convenient and less expensive compared to super-cooled systems such as with liquid nitrogen. Cryoprotectants are included when cells are frozen in order to prevent the damaging effects of water crystals. Similarly, desiccation requires anhydroprotectants to prevent destruction of bio-molecules as the water is removed during the preservation process.

Some anhydrobiotic organisms are actually able to survive in a nearly completely dry or desiccated state without freezing. Members of the tardigrades, for example, are capable of surviving under these conditions (Crowe and Cooper, 1971). These organisms are highly complex, with heads, limbs and internal body parts similar to those of insects. Anhydrobiosis is made possible, in large part, through the elaboration and distribution of a sugar, trehalose, which supports cellular membrane structure against collapse by substituting for water at the polar head groups of the lipids (Crowe and Crowe, 1991, Crowe et al., 1992; Leslie et al., 1995; Mansure et al., 1994). It has been suggested that trehalose has cryoprotective properties (Crowe et al., 1992; Israeli et al., 1993; Leslie et al., 1994). U.S. Pat. No. 5,059,518 and 5,409,826 describe the use of trehalose as a stabilizer for preserving human cells by lyophilization.

Chemically, trehalose is a non-reducing disaccharide consisting of two linked glucose molecules and has approximately half the sweetness of sucrose. Empirical evidence indicates that high concentrations of trehalose in the tissues of certain insects and desert plants allows them to survive in a state of suspended animation under conditions of water deficiency (Hirsh, 1987). It has also been suggested that trehalose is an important factor in the survival of frogs during the frozen winter months (Lee et al., 1992).

U.S. Pat No. 5,149,653 describes the use of trehalose in the preservation of viruses. Unlike mammalian cells, however, live virus vaccines can not be easily frozen without loosing their immunogenic effect. Therefore, they must either be kept in aqueous media under cool sterile conditions such as in a refrigerator or stored at room temperature in the presence of preserving agent such as trehalose.

Depending on the species, bacteria can be stored either at room temperature, refrigerated as slant cultures on nutrient agar, or frozen. Storage of bacteria on agar, for those species that will tolerate it, is relatively convenient. However, it has been shown that organisms can genetically alter over time, especially the genetic material which are carried on plasmids. Additionally, not all bacteria can be stored for long periods on nutrient agar. Although most bacteria can be frozen, like viruses and eukaryotic cells, some alterations to the bacteria can occur upon thawing. Furthermore, recovery rates of bacteria are variable among species and among freezing conditions. Also, the process for freezing of cells is often relatively complex, requiring either super-cooled systems such as liquid nitrogen or mechanical freezers. In some circumstances, especially field conditions or operations studies conducted in developing countries, the availability and maintenance of super-cooled systems or mechanical freezers, or even refrigerators, is often problematic.

The prior art identified addresses the use of trehalose in the preservation of mammalian cells by lyophilization or, in the case of viral viruses by evaporation at ambient temperatures. The use of trehalose for the preservation of bacteria, which have distinct membrane structure compared to mammalian cells or viruses is not previously described. Although many strains of bacteria can withstand freezing and drying in the absence of a special preserving agent, because of the presence of a rigid outer wall, the efficiency of recovery is often poor. Furthermore, many, more fragile bacteria, are incapable of being preserved without cryoprotective additives. The prior art does not lead to a simple, effective and easy to conduct method of bacterial preservation applicable for a large range of bacterial species not requiring equipment such as freezers or the availability of liquid nitrogen. Additionally, the use of divalent cations, in conjunction with trehalose, as stabilizing agents is not previously described.

SUMMARY OF THE INVENTION

Accordingly, an object of this invention is to provide a new, effective and economical process for the preservation of bacterial species without requiring special equipment beyond what is typically found in microbiology laboratories.

An additional object is that the bacteria can be easily reconstituted with a high rate of survival.

A further object is that the bacteria retain characteristics and are not detectably altered after freezing and reconstitution.

These and additional objects of the invention are accomplished by drying bacteria in the presence of the cryopreservative trehalose and more preferably in the presence of certain divalent cations. The method of preservation involves drying bacteria in the presence of specific cryopreservation materials such that the organisms can be reconstituted in a viable form with little or no genetic damage. This process is capable of being used on a number of different bacterial genera and species, beyond those immediately described here. Following preservation and reconstitution the cells retain their genotypic and phenotypic characteristics.

BRIEF DESCRIPTION OF THE DRAWINGS

A more complete appreciation of the invention will be readily obtained by reference to the following Description of the Preferred Embodiments and the accompanying FIGURE.

DESCRIPTION OF THE PREFERRED EMBODIMENTS

Figure 1:
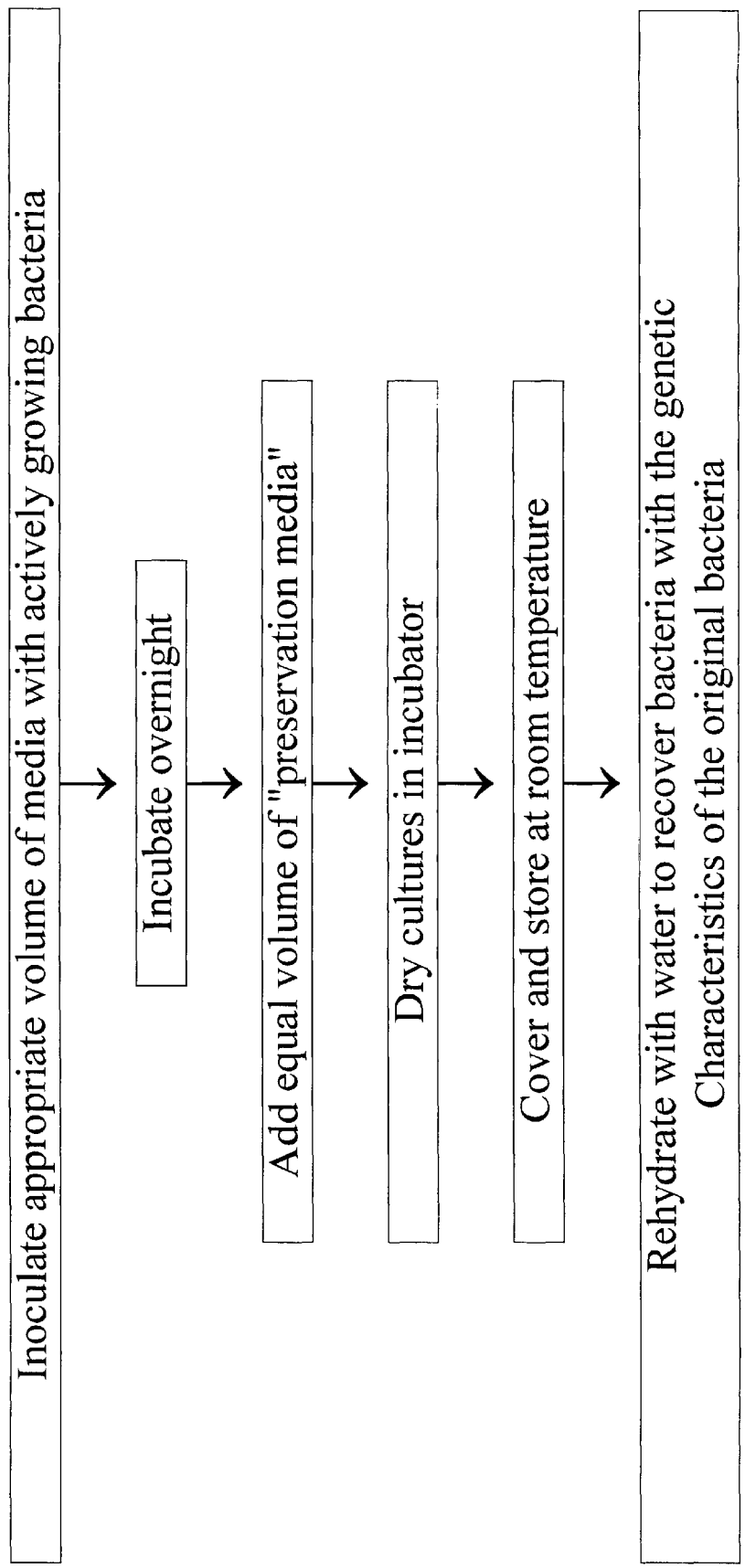
FIG. 1 is a diagrammatic presentation of the preservation methods.

The present invention can be utilized to preserve for short or long term storage or for transport, a large number of different bacterial genera and species. The process is easy to conduct, relatively inexpensive and does not require equipment outside of that normally encountered in a standard microbiology laboratory. The process, illustrated in FIG. 1, entails inoculating bacteria in a small volume of bacterial culture media common in the art and described in Manual of Clinical Microbiology, ASM. The type of media selected is dependent on the species of bacteria to be preserved. Some preparatory procedures are employed, prior to preservation. These include: 1) growth of bacteria on suitable agar or liquid broth; 2) harvesting of organisms by scraping colonies off of agar plates or collection from liquid cultures; 3) centrifugation of bacteria and resuspension in bacterial culture media at an appropriate concentration for expansion for preservation the following day. The bacterial cell density at harvesting depends on the bacterial species, however typical densities are 0.1 to 0.5 OD units. The preservation procedure is carried out the following day. After resuspension the bacteria are added to wells of a 96 well, or other type of suitable plate, and incubated overnight. Subsequent to the overnight incubation an equal volume of "preservation solution", containing from 10 mM to 200 mM trehalose with or without the addition of 1 to 10 mM one or more of the divalent cations Mg++, Ca++, 2n++, Mm++ (typically in forms such as $CaCl_2$, $ZnCl_2$, or $MgCl_2$) is added to the cultures, the cultures placed in an incubator, at 37° C. and allowed to dry completely over a period of up to 96 hours freezing is not involved. The dried cultures covered, sealed in protective bags or containers and stored at room temperature at 20° C. to 25° C.

Reconstitution of the bacteria is accomplished by the addition of sterile water equal to the original total volume, pre-warmed to growth temperatures (37° to 42° C.), depending on bacterial species being preserved, and then plated onto bacterial growth media.

Having described the invention, the following examples are given to illustrate specific applications of the invention including the best mode now known to perform the invention. These specific examples are not intended to limit the scope of the invention described in this application.

EXAMPLE 1

Evaluation of the Effect of Trehalose on the Preservation of Bacterial Strains at Room Temperature in the Dry State.
1. Bacterial Strains
Bacteria strains with the following phenotypic characteristics were each tested for their ability to be preserved and reconstituted using trehalose as preservation agent: *Escherichia coli* (W3110 Wild-type), *Vibrio cholera* (O139), *Salmonella typhimurium* LT2, and *Shigellaflexneri* 2a.
2. Preservation
The different strains of bacteria listed above were each individually inoculated into standard culture media in wells of a 96-well microtiter dish. They were grown overnight at 37° C. The following day an equal volume of preservation media, with 10 mM of each divalent cation ($CaCl_2$, $MgCl_2$ $ZnCl_2$), containing increasing concentrations of trehalose was added to the growing cultures giving a final concentration of trehalose from 10 mM to 200. The cultures were gently rocked over a 96 hour period and the contents allowed to dry. The dish was then covered and placed at room temperature.

3. Reconstitution
After 72 hours, individual cultures were rehydrated with sterile water, pre-warmed to 37° C. and added to Luria-Broth media to test for viability. The results are shown in Table 1. As shown in Table 1, with the exception of *E. coli*, all the species of bacteria tested had a higher level of viability after 72 hours when preserved in the presence of trehalose than without.

TABLE 1

| | 10 mM each of $CaCl_2$, $MgCl_2$ and $ZnCl_2$, plus | | | | | |
|---|---|---|---|---|---|---|
| Bacterial Strain | 10 | 25 | 50 | 100 | 150 | 200 (mM Trehalose) |
| *E. coli* (wild-type) | + | + | + | + | + | + |
| *Vibrio cholera* | − | +/− | + | + | + | + |
| *Salmonella typhimurium* | +/− | + | + | + | + | + |
| *Shigella flexneri* 2a | +/− | +/− | + | + | + | + |

EXAMPLE 2

Evaluation of the genotypic and phenotypic characteristics of bacterial strains affer cryopreservation with trehalose and the divalent cations; $CaCl_2$, $MgCl_2$, and $ZnCl_2$.
1. Bacterial Strains
*E. coli* strains with the following phenotypic characteristics were each tested for their ability to be preserved and reconstituted using trehalose as preservation agent: Wild-type, ETEC:LT, ETEC:ST, ETEC:LT/ST, Vibrio cholerae O139, *Salmonella typhimurium* LT2, *Shigella flexneri* 2a.
2. Preservation
The different strains of bacteria listed above were each individually inoculated into standard culture media in wells of a 96-well microtiter dish. They were grown overnight at 37° C. The following day an equal volume of preservation media containing increasing concentrations of trehalose was added to the growing cultures giving a final concentration of trehalose from 10 mM to 200. The cultures were gently rocked over a 96 hour period and the contents allowed to dry. The dish was then covered and placed at room temperature.
3. Reconstitution
At regular intervals, up to 120 days, individual cultures were rehydrated with sterile water, pre-warned to 37° C. and added to brain-heart infusion broth (BHIB). The results of the bacterial viability are shown in Table 2 at 100 mM trehalose and 10 mM each of $ZnCl_2$, $CaCl_2$, and $MgCl_2$.
4. Phenotypic/genotypic Analysis
After growing overnight in BHIB, the individual colonies were tested for their ability to grow on selective media, and for the presence of genetic markers by polymerase chain reaction. The colonies were also tested for identity by API20E biochemical test strips. The results of these analyses are shown in Table 2.

TABLE 2

| | Media | | | | |
|---|---|---|---|---|---|
| Organism | MAC | M9 | TCBS | API20E | PCR |
| *E. coli* W3110 (wild-type) | + | + | NA | + | NA |
| *E. coli* (ETEC:LT) | + | NA | NA | + | + |
| *E. coli* (ETEC:ST) | + | NA | NA | + | + |
| *E. coli* (ETEC:LT/ST) | + | NA | NA | + | + |
| *Vibrio cholerae* (O139) | NA | NA | + | + | + |
| *Salmonella typhimurium* (LT2) | + | NA | NA | + | + |

TABLE 2-continued

| | Media | | | | |
|---|---|---|---|---|---|
| Organism | MAC | M9 | TCBS | API20E | PCR |
| *Shigella flexneri* 2a | + | NA | NA | + | + |

The examples given are average results from a number of experiments which demonstrate that cryopreservation in the presence of trehalose and the divalent cations permit storage of different bacterial species and strains with no detectable phenotypic alteration.

References

1. U.S. Pat. No. 5,059,518 October 1991 Kortright et al . . .
2. U.S. Pat. No. 5,149,653 September 1992 Roser . . .
3. U.S. Pat. No. 5,409,826 June 1993 Maples et al . . .
4. Carpenter, et al., *Biochim. Biophys. Acta* 923, 109–115, 1987
5. Carpenter, et al., *Cyrobiol.* 25, 372–376, 1988
6. Oliver, et al., *Biochim. Biophys. Acta* 1267, 92–100, 1995
7. Roser, *BioParm, September*, 47–53, 1991
8. Shier, *Cryobiol.* 25, 110–120, 1988
9. Crowe and Crowe, *Devel. Biol. Stand.* 74, 285–294, 1991
10. Crowe et al., *Ann. Rev. Physiol.* 54, 579–599, 1992
11. Crowe and Cooper, *Scientific American* 225, 30–36, 1971
12. Leslie et al., *Appl. Environ. Microbiol.* 61,3592–3597, 1995
13. Mansure et al., *Biochim. Biophys. Acta* 1191, 309–316, 1994
14. Israeli et al., *Cyrobiol.*, 30, 519–523, 1993
15. Leslie et al., *Biochim. Biophys. Acta*, 1192, 7–13, 1994
16. Hirsh, *Cryobiol.*, 24, 214–228, 1987
17. Lee et al., *J. Therm. Biol.*, 17, 263–266, 1992
18. Manual of Clinical Microbiology, 6 th Ed., Amer. Soc. of Mircro., Ed. In Chief, Albert Ballows Obviously, many modifications and variations of the present invention are possible in light of the above teachings. It is therefore to be understood that, within the scope of the appended claims, the invention may be practiced otherwise than as specifically described.

What is claimed is:

1. A dried composition for the preservation of aerobic bacteria in a viable state wherein said dried composition consists essentially of: dried viable aerobic bacteria and growth medium appropriate for the bacteria, wherein said composition is prepared by placing said aerobic bacteria and growth medium in an aqueous solution containing 10 mM to 200 mM trehalose and a divalent cation and drying the solution at room temperature.

2. The dried composition of claim 1 wherein the divalent cation is selected from the group consisting of $CaCl_2$, $ZnCl_2$, $MgCl_2$ and combinations of those divalent cations.

3. The dried composition of claim 1, wherein said bacteria is gram-negative.

4. The dried composition of claim 3, where said gram-negative bacteria is wild-type *E.coli.*

5. The dried composition of claim 3, where said gram-negative bacteria is *Vibrio cholera.*

6. The dried composition of claim 3, where said gram-negative bacteria is *Salmonella typhimurium.*

7. The dried composition of claim 3, where said gram-negative bacteria is *Shigella flexneri* 2a.

8. A method of preserving aerobic bacterial species in a viable state at room temperature comprising:

(a) Inoculating the aerobic bacteria that is to be preserved in a volume of suitable bacterial culture medium;

(b) Growing the living aerobic bacteria at its optimal growth temperature to increase volume;

(c) Harvesting the aerobic bacteria;

(d) Separating the aerobic bacteria from the growth medium;

(e) Re-suspending the aerobic bacteria in fresh growth medium;

(g) Incubating the aerobic bacteria at least over-night at incubation temperatures appropriate for the bacteria;

(h) Adding to the incubated aerobic bacteria of step (g) an equal volume of a preservation solution consisting essentially of an aqueous solution of 10 mM to 200 mM of trehalose and a divalent cation selected from the group consisting of $CaCl_2$, $ZnCl_2$, $MgCl_2$ and combinations thereof;

(i) Drying the combination of aerobic bacteria and preservation solution of step (h) at about 37° C.;

(j) Recovering and storing the dried aerobic bacteria in sealed containers at room temperature until such time as needed; and (k) Restoring the aerobic bacteria to a viable state by rehydration of the dried aerobic bacteria with water.

9. The method of claim 8, wherein said bacteria is gram-negative.

10. The method of claim 9, wherein said gram-negative bacteria is wild-type *E.coli.*

11. The method of claim 9, wherein said gram-negative bacteria is *Vibrio cholera.*

12. The method of claim 9, wherein said gram-negative bacteria is *Salmonella typhimurium.*

13. The method of claim 9, wherein said gram-negative bacteria is *Shigella flexneri* 2a.

* * * * *